United States Patent
Ramachandran et al.

(10) Patent No.: US 12,071,393 B2
(45) Date of Patent: Aug. 27, 2024

(54) AMINE-BORANES AS BIFUNCTIONAL REAGENTS FOR DIRECT AMIDATION OF CARBOXYLIC ACIDS

(71) Applicant: Purdue Research Foundation, West Lafayette, IN (US)

(72) Inventors: Padinjaremadhom V. Ramachandran, West Lafayette, IN (US); Henry J. Hamann, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/407,276

(22) Filed: Aug. 20, 2021

(65) Prior Publication Data

US 2022/0055983 A1     Feb. 24, 2022

Related U.S. Application Data

(60) Provisional application No. 63/068,390, filed on Aug. 21, 2020.

(51) Int. Cl.

| | |
|---|---|
| *C07C 231/02* | (2006.01) |
| *C07C 233/05* | (2006.01) |
| *C07C 233/08* | (2006.01) |
| *C07C 233/58* | (2006.01) |
| *C07C 233/65* | (2006.01) |
| *C07C 323/41* | (2006.01) |
| *C07D 213/82* | (2006.01) |
| *C07D 295/192* | (2006.01) |
| *C07F 5/02* | (2006.01) |

(52) U.S. Cl.
CPC .......... *C07C 231/02* (2013.01); *C07C 233/05* (2013.01); *C07C 233/08* (2013.01); *C07C 233/58* (2013.01); *C07C 233/65* (2013.01); *C07C 323/41* (2013.01); *C07D 213/82* (2013.01); *C07D 295/192* (2013.01); *C07F 5/027* (2013.01)

(58) Field of Classification Search
CPC ...................................................... C07F 5/027
See application file for complete search history.

(56) References Cited

PUBLICATIONS

American Chemical Society. Chemical Abstract Service. RN 28987-40-8. First entered into STN/date of first public availability: Nov. 16, 1984. (Year: 1984).*
Hamann, Henry, et al. "Amine-boranes as Dual-Purpose Reagents for Direct Amidation of Carboxylic Acids." Org. Lett. (2020), vol. 22, pp. 8593-8597. (Year: 2020).*
Pelter, A. and T.E. Levitt. "Investigation of the Mechanisms of the Amide Forming Reactions of Trisdialkylaminoboranes." Tetrahedron. (1970), vol. 26, pp. 1899-1908. (Year: 1970).*
Brown, D. G., Bostrom, J., Analysis of Past and Present Synthetic Methodologies on Medicinal Chemistry: Where Have All the New Reactions Gone? J. Med. Chem. 2016, 59, 4443-58.
Charville, H., Jackson, D. A., Hodges, G., Whiting, A., Wilson, M. R., The Uncatalyzed Direct Amide Formation Reaction—Mechanism Studies and the Key Role of Carboxylic Acid H-Bonding Eur. J. Org. Chem. 2011, 2011, 5981-5990.
Jursic, B. S., Zdravkovski, Z., A Simple Preparation of Amides from Acids and Amines by Heating of Their Mixture Synth. Commun. 1993, 23, 2761-2770.
Bryan, M. C., Dunn, P. J., Entwistle, D., Gallou, F., Koenig, S. G., Hayler, J. D.; , Hickey, M. R., Hughes, S., Kopach, M. E., Moine, G., Richardson, P., Roschangar, F., Steven, A., Weiberth, F. J., Key Green Chemistry Research Areas from a Pharmaceutical Manufacturers' Perspective Revisited Green Chem. 2018, 20, 5082-5103.
Pattabiraman, V. R., Bode, J. W., Rethinking Amide Bond Synthesis Nature 2011, 480, 471-479.
Tang, P., Boric Acid Catalyzed Amide Formation from Carboxylic Acids and Amines: N-Benzyl-4-Phenylbutyramide Org. Synth. 2005, 81.
Hall, D. G., Boronic Acid Catalysis Chem. Soc. Rev. 2019, 48, 3475-3496.
Ishihara, K., Ohara, S., Yamamoto, H., 3,4,5-Trifluorobenzeneboronic Acid as an Extremely Active Amidation Catalyst J. Org. Chem. 1996, 61, 4196-4197.
Sabatini, M. T., Boulton, L. T., Sheppard, T. D., Borate Esters: Simple Catalysts for the Sustainable Synthesis of Complex Amides Sci. Adv. 2017, 3.
Huang, Z., Reilly, J., Buckle, R., An Efficient Synthesis of Amides and Esters via Triacyloxyboranes Synlett 2007, 2007, 1026-1030.
Ramachandran, P. V., Drolet, M. P., Kulkarni, A. S., A Non-Dissociative Open-Flask Hydroboration with Ammonia Borane: Ready Synthesis of Ammonia-Trialkylboranes and Aminodialkylboranes Chem. Comm. 2016, 52, 11897-11900.
Rodriguez, J. R., Hamann, H. J., Mitchell, G. M., Ortalan, V., Pol, V. G., Ramachandran, P. V., Three-Dimensional Antimony Nanochains for Lithium-Ion Storage ACS Appl. Nano Mater. 2019, 2, 5351-5355.
Ramachandran, P. V., Kulkarni, A. S., Water-Promoted, Safe and Scalable Preparation of Ammonia Borane Int. J. Hydrog. Energy 2017, 42, 1451-1455.
Ramachandran, P. V.,,Kulkarni, A. S.,,Zhao, Y., Mei, J., Amine-Boranes Bearing Borane-Incompatible Functionalities: Application to Selective Amine Protection and Surface Functionalization Chem. Comm. 2016, 52, 11885-11888.
Tao, Y.,, Widlicka, D. W., Hill, P. D.,,Couturier, M., Young, G. R., A Scalable Synthesis of Ce-157119 Hcl Salt, an Sri/5-Ht2a Antagonist Org. Process Res. Dev. 2012, 16, 1805-1810.
Montalbetti, C.,,Falque, V., Amide Bond Formation and Peptide Coupling Tetrahedron 2005, 61, 10827-10852.

\* cited by examiner

*Primary Examiner* — John S Kenyon
(74) *Attorney, Agent, or Firm* — Purdue Research Foundation

(57) ABSTRACT

The present invention generally relates to a process for selective and direct activation and subsequent amidation of aliphatic and aromatic carboxylic acids to afford an amide $R^3CONR^1R^2$. That the process is capable of delivering gaseous or low-boiling point amines provides a major advantage over existing methodologies, which involves an intermediate of triacyloxyborane-amine complex $[(R^3CO_2)_3$—B—$NHR^1R^2]$. This procedure readily produces primary, secondary, and tertiary amides, and is compatible with the chirality of the acid and amine involved. The preparation of known pharmaceutical molecules and intermediates has also been demonstrated.

4 Claims, 4 Drawing Sheets

AMINE-BORANES AS BIFUNCTIONAL REAGENTS FOR DIRECT AMIDATION OF CARBOXYLIC ACIDS

CROSS-REFERENCE TO RELATED APPLICATIONS

The present U.S. patent application relates to and claims the priority benefit of U.S. Provisional Patent Application Ser. No. 63/068,390, filed Aug. 21, 2020, the contents of which are hereby incorporated by reference in its entirety into this disclosure.

TECHNICAL FIELD

The present invention generally relates to a process for direct preparation of amides from the corresponding carboxylic acids. More specifically, this disclosure provides a method for selective and direct activation and subsequent amidation of aliphatic and aromatic carboxylic acids. That the process is capable of delivering gaseous or low-boiling point amines provides a major advantage over existing methodologies. This procedure readily produces primary, secondary, and tertiary amides, and is compatible with chirality in the acid and amine. The preparation of known pharmaceutical molecules and intermediates has also been demonstrated.

BACKGROUND AND SUMMARY OF THE INVENTION

This section introduces aspects that may help facilitate a better understanding of the disclosure. Accordingly, these statements are to be read in this light and are not to be understood as admissions about what is or is not prior art.

The ubiquity of amides in natural and synthetic biologically active molecules makes amidation as one of the predominant reactions in the landscape of modern medicinal chemistry.[1,2] Additionally, amides find important applications in the polymer,[3-6] adhesive,[7] and agrochemical industries.[8] The seemingly simple synthesis of amides from carboxylic acids and amines, direct amidation, is however, inhibited by the formation of unreactive ammonium carboxylates.[9-12] Overcoming the thermodynamic barrier of the salt formation requires harsh reaction conditions and has landed direct amidation among the highly challenging reactions identified by the ACS Green Chemistry Institute Pharmaceutical Roundtable.[13] Accordingly, there is considerable activity in this area of research[14,15] and several stoichiometric and catalytic methodologies have been reported.[16] The utility of organoboranes for amidation has been examined for nearly five decades since Pelter's report on the use of trisdialkylaminoboranes.[17] Boron-containing catalysts/activators such as catecholborane,[18] boric acid,[19] boronic acids,[20,21] borate esters,[22] borane-tetrahydrofuran,[23] and boron trifluoride-diethyl etherate[24] are particularly noteworthy for their application to direct amidation.

The present invention generally relates to a process for direct preparation of amides from the corresponding carboxylic acids. More specifically, this disclosure provides a method for selective and direct activation and subsequent amidation of aliphatic and aromatic carboxylic acids. These and other features, aspects and advantages of the present invention will become better understood with reference to the following detailed description and claims.

BRIEF DESCRIPTION OF DRAWINGS

The above and other objects, features, and advantages of the present invention will become more apparent when taken in conjunction with the following description and drawings wherein identical reference numerals have been used, where possible, to designate identical features that are common to the figures, and wherein.

DETAILED DESCRIPTION

Figure 1:
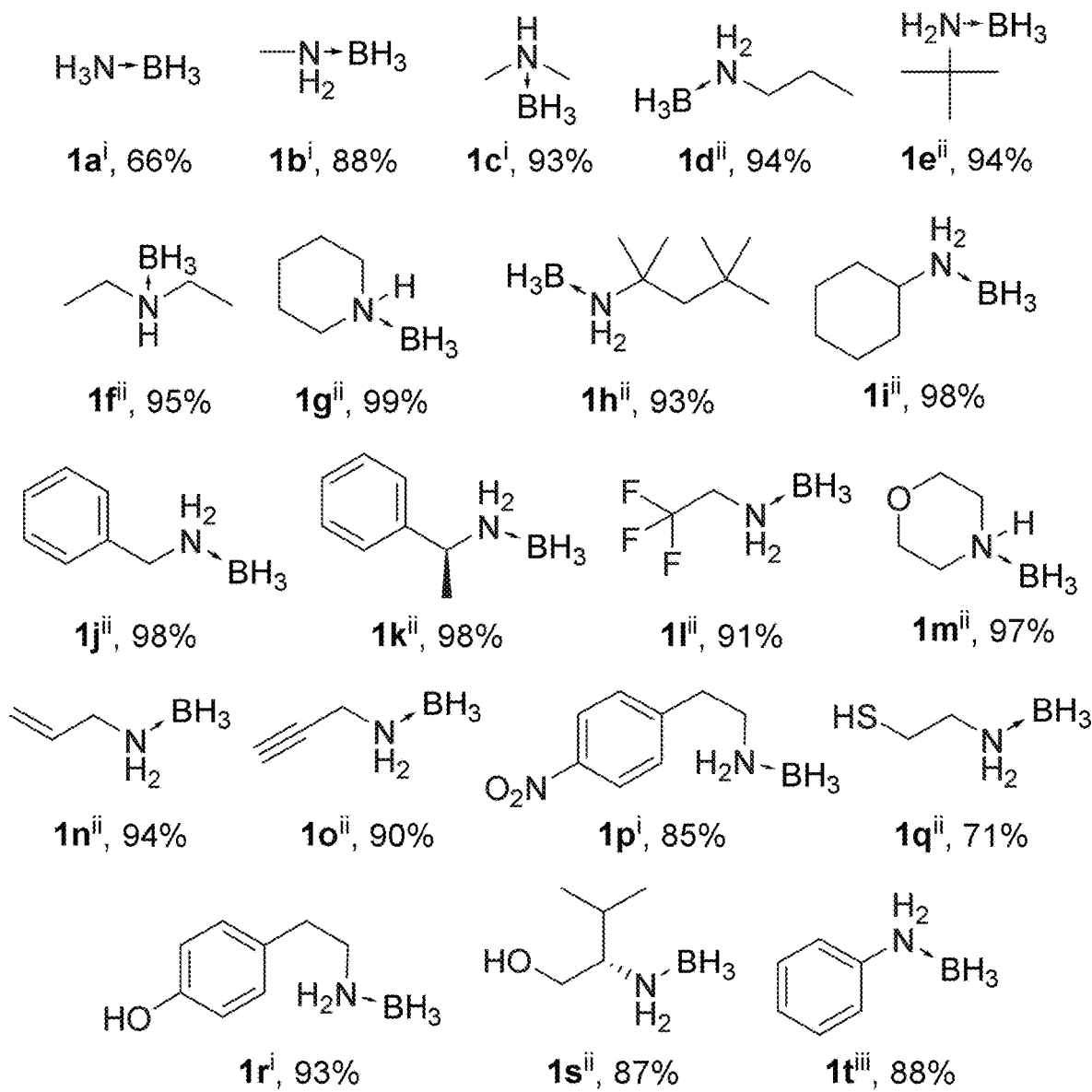
FIG. 1 shows the scope of amine-boranes applied in this study, prepared via (i) salt metathesis (ii) $NaHCO_3$ mediated reaction of $NaBH_4$ with free amine, or (iii) Lewis-base displacement using borane dimethyl sulfide.

While the concepts of the present disclosure are illustrated and described in detail in the description herein, results in the description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. As used herein, the term "alkyl" encompasses n-alkyl, isoalkyl, tertiary-alkyl, and cycloalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3+$, wherein each R is independently selected, and protonated forms of each, except for —$NR_3+$, which cannot be protonated. Accordingly, any compound substituted with an amino group can be viewed as an amine. An "amino group" within the meaning herein can be a primary, secondary, tertiary, or quaternary amino group. An "alkylamino" group includes a mono alkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluorine. Examples of haloalkyl include trifluoromethyl, 1,1-dichloroethyl, 1,2-dichloroethyl, 1,3-dibromo-3,3-difluoropropyl, perfluorobutyl, —$CF(CH_3)_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

In some illustrative embodiments, this disclosure relates to a process for direct activation and subsequent amidation of an aliphatic or an aromatic carboxylic acid to manufacture an amide $R^3CONR^1R^2$, comprising the steps of a. preparing an amine-borane $R^1R^2NH$—$BH_3$ from an amine $R^1R^2NH$; wherein $R^1$ and $R^2$ are, independently, hydrogen, an alkyl, or an aryl, wherein said alkyl or aryl are optionally substituted and said $R^1$ and $R^2$ are not both an aryl or a hydrogen at the same time;

b. preparing a carboxylic acid $R^3COOH$, wherein $R^3$ is an alkyl or an aryl, each of which is optionally substituted;

c. dissolving one equivalent of said amine-borane and about three equivalents of said carboxylic acid in xylenes or a compatible solvent to afford a reaction mixture;

d. first heating said reaction mixture to about 90-100° C. for about 1 hour, then raising the temperature to about 150° C. for about 12 hours; and e. resolving said reaction mixture to afford said amide $R^3CONR^1R^2$ together with recovered excess carboxylic acid $R^3COOH$.

In some illustrative embodiments, this disclosure relates to a process for direct activation and subsequent amidation of an aliphatic or an aromatic carboxylic acid to manufacture an amide $R^3CONR^1R^2$ as disclosed herein, wherein said optionally substituted alkyl or aryl may comprises one or more heteroatoms selected from the group consisting of B, N, O, S, Se, Cl, Br, F, I, Si, As, Te, Ge, or a combination thereof.

In some illustrative embodiments, this disclosure relates to a process for direct activation and subsequent amidation of an aliphatic or an aromatic carboxylic acid to manufacture an amide $R^3CONR^1R^2$ as disclosed herein, wherein said optionally substituted alkyl or aryl comprises one or more functional groups selected from the group consisting of hydroxyl, thiol, cyano, halo, ether, cyclic ether, sulfide, cyclic sulfide, tertiary amine, ester, cyclic ester (lactone), alkenyl, alkynyl, aryl, heteroaryl, phenol, silyl ether, nitro, amide, cyclic amide (lactam), or a combination thereof.

In some illustrative embodiments, this disclosure relates to a process for direct activation and subsequent amidation of an aliphatic or an aromatic carboxylic acid to manufacture an amide $R^3CONR^1R^2$ as disclosed herein, wherein said amide is a primary, a secondary, or a tertiary amide.

In some illustrative embodiments, this disclosure relates to a process for direct activation and subsequent amidation of an aliphatic or an aromatic carboxylic acid to manufacture an amide $R^3CONR^1R^2$ as disclosed herein, said process comprises an intermediate of triacyloxyborane-amine complex $[(R^3CO_2)_3—B—NHR^1R^2]$, wherein $R^3$ is an alkyl or an aryl, each of which is optionally substituted; $R^1$ and $R^2$ are, independently, hydrogen, an alkyl, or an aryl, wherein said alkyl or aryl are optionally substituted and said $R^1$ and $R^2$ are not both an aryl or a hydrogen at the same time.

In some illustrative embodiments, this disclosure relates to a process for direct activation and subsequent amidation of an aliphatic or an aromatic carboxylic acid to manufacture an amide $R^3CONR^1R^2$ as disclosed herein, wherein said optionally substituted alkyl or aryl comprises one or more heteroatoms selected from the group consisting of B, N, O, S, Se, Cl, Br, F, I, Si, As, Te, Ge, or a combination thereof.

In some illustrative embodiments, this disclosure relates to a process for direct activation and subsequent amidation of an aliphatic or an aromatic carboxylic acid to manufacture an amide $R^3CONR^1R^2$ as disclosed herein, wherein said optionally substituted alkyl or aryl may comprises one or more functional groups selected from the group consisting of hydroxyl, thiol, cyano, halo, ether, cyclic ether, sulfide, cyclic sulfide, tertiary amine, ester, cyclic ester (lactone), alkenyl, alkynyl, aryl, heteroaryl, phenol, silyl ether, nitro, amide, cyclic amide (lactam), or a combination thereof.

In some illustrative embodiments, this disclosure relates to a process for direct activation and subsequent amidation of an aliphatic or an aromatic carboxylic acid to manufacture an amide $R^3CONR^1R^2$ as disclosed herein, wherein said process is capable of delivering a gaseous or low-boiling point amine for direct manufacturing of an amide using a carboxylic acid.

In some illustrative embodiments, this disclosure relates to a process for direct activation and subsequent amidation of an aliphatic or an aromatic carboxylic acid to manufacture an amide $R^3CONR^1R^2$ as disclosed herein, wherein said process is compatible with a chirality in said acid or said amine.

In some illustrative embodiments, this disclosure relates to an amide $R^3CONR^1R^2$ manufactured according to a process disclosed herein.

In some other illustrative embodiments, this disclosure relates to a triacyloxyborane-amine complex comprising $[(R^3CO_2)_3—B—NHR^1R^2]$, wherein $R^3$ is an alkyl or an aryl, each of which is optionally substituted; $R^1$ and $R^2$ are, independently, hydrogen, an alkyl, or an aryl, wherein said alkyl or aryl are optionally substituted and said $R^1$ and $R^2$ are not both an aryl or a hydrogen at the same time.

In some other illustrative embodiments, this disclosure relates to a triacyloxyborane-amine complex comprising $[(R^3CO_2)_3—B—NHR^1R^2]$, wherein said triacyloxyborane-amine complex $[(R^3CO_2)_3—B—NHR^1R^2]$ is manufactured as following:

a. preparing an amine-borane $R^1R^2NH—BH_3$ from an amine $R^1R^2NH$; wherein $R^1$ and $R^2$ are, independently, hydrogen, an alkyl, or an aryl, wherein said alkyl or aryl are optionally substituted and said $R^1$ and $R^2$ are not both an aryl or a hydrogen at the same time;

b. preparing a carboxylic acid $R^3COOH$, wherein $R^3$ is an alkyl or an aryl, each of which is optionally substituted;

c. dissolving one equivalent of said amine-borane and about three equivalents of said carboxylic acid in xylenes or a compatible solvent to afford a reaction mixture; and d. heating said reaction mixture to about 90-100° C. for about 1 hour to afford said triacyloxyborane-amine complex $[(R^3CO_2)_3—B—NHR^1R^2]$.

In some other illustrative embodiments, this disclosure relates to a triacyloxyborane-amine complex comprising $[(R^3CO_2)_3—B—NHR^1R^2]$, wherein said optionally substituted alkyl or aryl may comprises one or more heteroatoms selected from the group consisting of B, N, O, S, Se, Cl, Br, F, I, Si, As, Te, Ge, or a combination thereof.

In some other illustrative embodiments, this disclosure relates to a triacyloxyborane-amine complex comprising $[(R^3CO_2)_3—B—NHR^1R^2]$, wherein said optionally substituted alkyl or aryl may comprises one or more functional groups selected from the group consisting of hydroxyl, thiol, cyano, halo, ether, cyclic ether, sulfide, cyclic sulfide, tertiary amine, ester, cyclic ester (lactone), alkenyl, alkynyl, aryl, heteroaryl, phenol, silyl ether, nitro, amide, cyclic amide (lactam), or a combination thereof.

In some other illustrative embodiments, this disclosure relates to an active pharmaceutical ingredient manufactured using the triacyloxyborane-amine complex comprising $[(R^3CO_2)_3—B—NHR^1R^2]$ as disclosed herein.

Our involvement in the synthesis and applications of amine-boranes for both organic[25] and materials chemistry[26] drew us to this important reaction. Trapani's report on the N-acylation/alkylation of amines by carboxylic acids in the presence of a stoichiometric amount of trimethylamine-borane catalyst[27] provided the stimulus to further examine amine-boranes for amidation. Their experimental conditions enabled the formation of a triacyloxyborane, permitting a primary or secondary amine to approach the carbonyl for acyl substitution.

Based on this, we envisioned a direct amidation of carboxylic acids with amine-borane complexes containing non-tertiary amines. Our hypothesis was that the utilization of amine-boranes for amidation could serve the dual purpose of activating carboxylic acids to form the triacyloxyborane intermediates, and subsequently deliver the coordinated amine as the nucleophile, an impossibility when utilizing trimethylamine-borane.[27] We had particular interest in introducing low-boiling and gaseous amines as their amine-borane complexes, since existing procedures can only be readily applied to amines with boiling points high enough to tolerate the temperature of the reaction. Herein, we report a highly versatile direct amidation of carboxylic acids using amine-boranes as both activators and amine carriers. This methodology is capable of producing primary, secondary, and tertiary amides with a range of functionalities on the acid and amine used (Scheme 1).

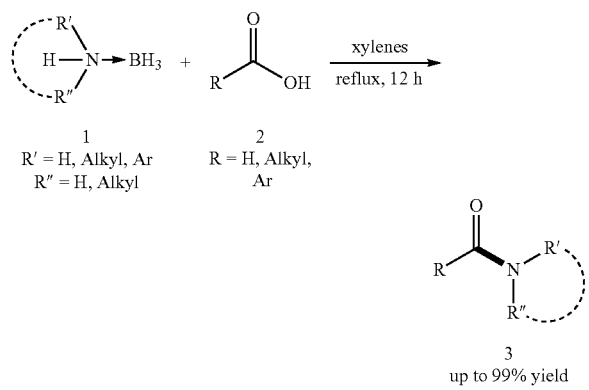

Scheme 1. Amidation of carboxylic acid using amine-boranes

The amine-boranes required to evaluate the scope of this reaction were produced from sodium borohydride using two methods (FIG. 1). (i) Gaseous and low-boiling amines, or those on-hand as ammonium salts, were converted to their corresponding amine-borane complexes (1a-d, p, r) by a salt metathesis reaction.[28,29] (ii) The remainder of the amines, apart from aniline, were converted to the amine-borane complex (1e-o, q, s) by using an aqueous sodium bicarbonate promoted reaction of the free amine.[30] These methods of amine-borane synthesis are less amenable to arylamines, therefore 1t was produced by a Lewis-base displacement reaction with borane dimethyl sulfide.[31]

Preliminary investigations towards the development of the amidation reaction were performed using benzoic acid (2a) and methylamine-borane (1b). Under optimized conditions, 3 equiv. of carboxylic acid (2) react with 1 equiv. of amine-borane (1) in refluxing xylenes (1 M in carboxylic acid) affording the corresponding amide (3) in yields up to 99% (FIG. 2), with complete recovery of the excess acid. Other aprotic solvents (toluene, cyclohexane, tetrahydrofuran) were tested, but reactions in solvents with boiling points lower than that of toluene drastically reduced amide recovery. The reaction requires no azeotropic removal of water or use of dehydrating agents.

Figure 2:
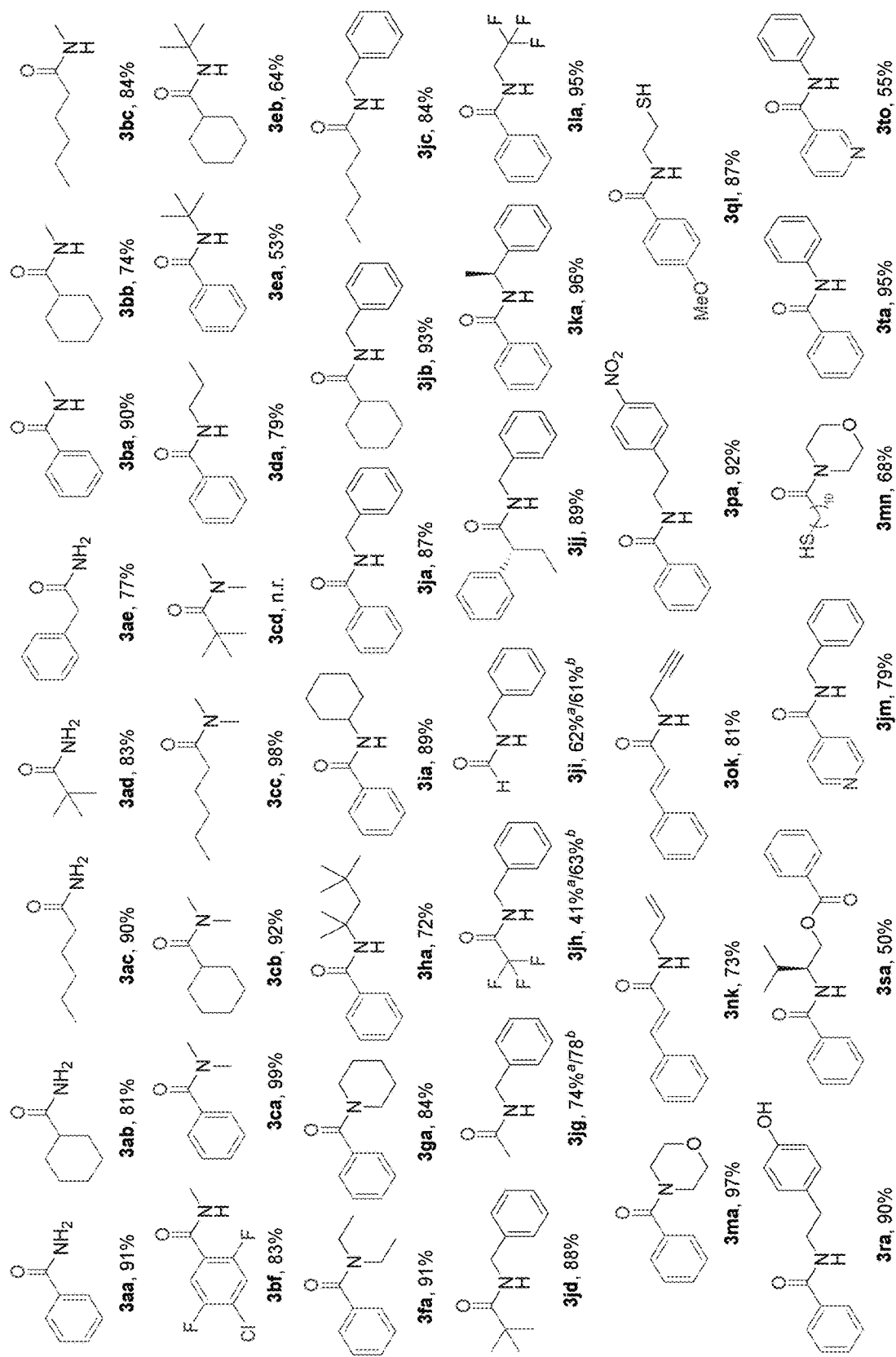
FIG. 2 depicts the structures of carboxamides prepared using amine-boranes; the first letter of the compound designation numbers identifies the amine-borane used in the preparation and the second letter indicates the carboxylic acid. $^a$3 equivalents of acid used, $^b$5 equivalents of acid used.

The reaction of ammonia-borane (1a) with both aromatic benzoic acid (2a) and aliphatic carboxylic acids (cyclohexanecarboxylic acid (2b), hexanoic acid (2c), pivalic acid (2d), phenylacetic acid (2e)) afforded the corresponding 1°-amides (3aa, 3ab, 3ac, 3ad, and 3ae, respectively) in 77-91% yields (FIG. 2). Borane complexes of other gaseous amines: methylamine (1b) and dimethylamine (1c), with acids 2a, 2b, 2c, and 2f (4-chloro-2,5-difluorobenzoic acid), provided the corresponding 2°-(3ba, 3bb, 3bc, and 3bf, respectively) and 3°-(3ca, 3cb, and 3cc, respectively) amides in 92-99% yields. Amide 3bf, prepared from 1b and 4-chloro-2,5-difluorobenzoic acid (2f), is a critical pharmaceutical intermediate[32] for the production of CE-157119 HCl salt.

Amide products containing a wide range of N-substitutions were obtained in 53-91% yield from either 2a or 2b, demonstrating the reaction's compatibility with aliphatic 1°-amines with 1°-(3da), 2°-(3ia), or 3°-(3ea, 3eb, 3ha) alkyl substituents, as well as acyclic (3fa) and cyclic (3ga) 2°-amines. The reduced yields of 3ea (53%), 3eb (64%), and 3ha (72%) can be attributed to the steric bulk of the triacyloxyborane-amine complex formed when using either 1e or 1h. A reaction of 1c with 2d could form the triacyloxyborane-amine intermediate 4cd (Scheme 2) but yielded none of the desired product 3cd.

Aromatic (2a) and 1°-, 2°-, and 3°-alkyl aliphatic (2c, 2b, and 2d) acids were also treated with benzylamine-borane (1j) yielding amide products 3ja-3jd. Amides 3jg, from acetic acid (2g), 3jh from 2,2,2-trifluoroacetic acid (2h), and 3ji from formic acid (2i) gave decreased yields of 74%, 41%, and 62% respectively, attributed to the relatively low boiling point of the acids. When reactions were performed using 5 equivalents of acid, the yield increased to 78% for 3jg and 63% for 3jh. However, no increase in yield for 3ji was observed. The reaction of 2-phenylbutanoic acid (2j) with 1j and benzoic acid (2a) with α-methylbenzylamine-borane (1k) proceeded smoothly, yielding the corresponding amides 3jj and 3ka in 89% and 96% yields, respectively.

Having achieved the reaction of both aliphatic and aromatic carboxylic acids with ammonia and a series of 1°- and 2°-amines containing variously substituted alkyl groups, compatibility of a variety of functionalized amine-boranes was tested. The trifluoromethyl-containing amine-borane 1l produced the amide 3la in 95% yield. Preparation of amide 3ma in 97% yield demonstrates the compatibility of heterocyclic amine-boranes. Multiple bond containing amine-boranes 1n and 1o, were well tolerated. Cinnamic acid (2k) produced amides 3nk and 3ok in 81% and 73% yields respectively, although a small amount (~5-10%) of the amide in which the double bond of 2k had been hydrogenated was also detected in each case. The use of amine-borane 1p containing a nitro moiety delivered amide 3pa in 92% yield with no reduction of the nitro group. Amides 3ql and 3ra were synthesized using amine-boranes containing additional nucleophilic groups. Reactions of thiol- (1q) and phenol-containing (1r) amine-boranes with either 2a or p-methoxybenzoic acid (2l) yielded the corresponding amides with no thioester formation in the case of 3ql nor ester formation in the cases of 3ra. However, the reaction of an aliphatic amino alcohol (L-valinol)-borane (1s) with 2a provided 50% of product 3sa, resulting from simultaneous esterification and amidation.

Examination of the compatibility of a nucleophile on the carboxylic acids led to interesting observations. The presence of the hydroxyl group in mandelic acid and 4-hydroxybenzoic acid was detrimental to product formation due to a competing alkoxyborane formation. However, amine-bearing carboxylic acids result in amine-exchange with the amine-borane reagent. Thus, the reaction of isonicotinic acid (2m) with 1a results in the liberation of ammonia and, consequently, no product formation. Utilizing the amine-borane from a higher boiling amine, eg. 1j, however, led to the formation of the amide 3jm in 79% yield. A reaction of thiol-containing 11-mercaptoundecanoic acid (2n) with 1m gave 68% of product (3mn).

The amidation protocol was then extended to include arylamine-boranes. Aniline-borane (1t) reacts with 2a and nicotinic acid (2o) to provide the corresponding amide, 3ta and 3 to in 95% and 55% yields respectively.

Figure 3:
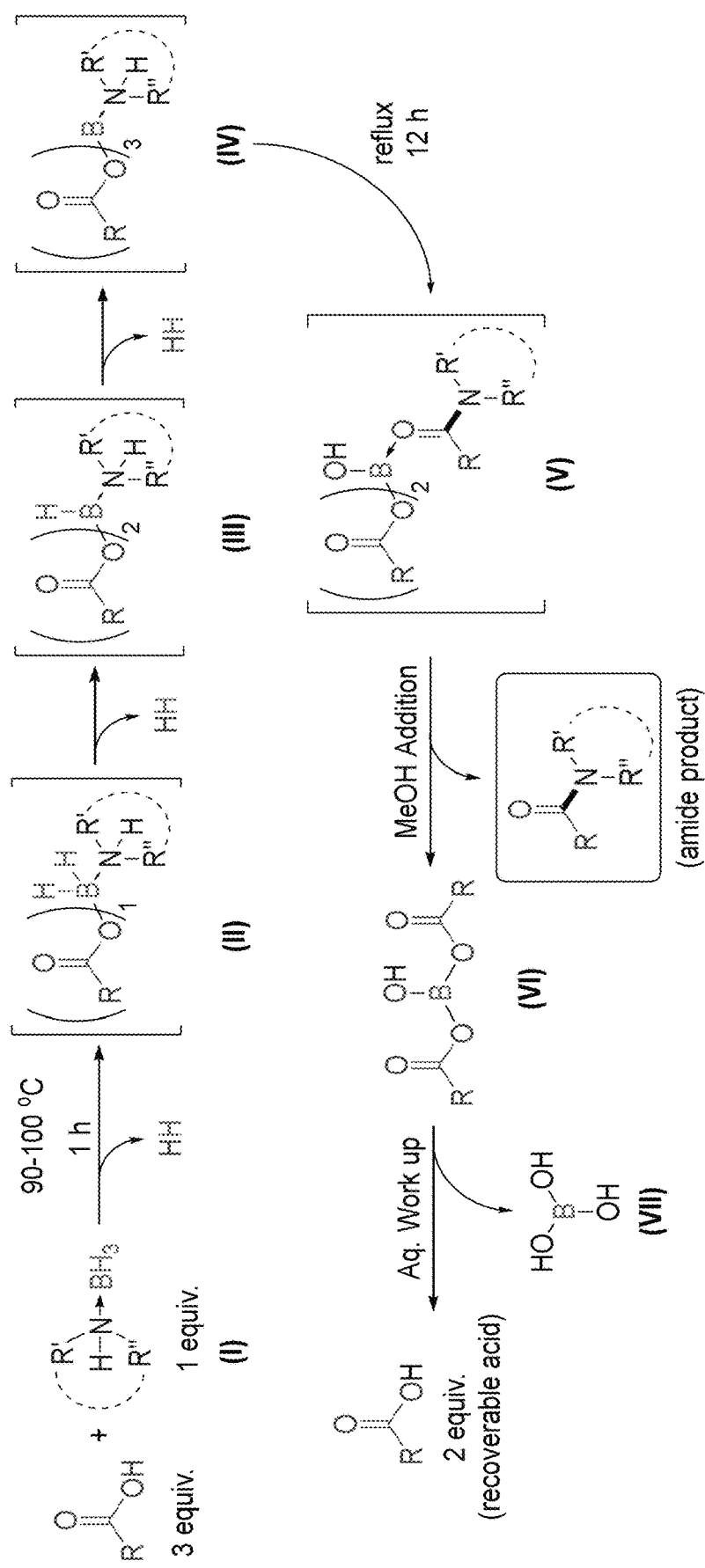
FIG. 3 shows the proposed reaction mechanism with a triacyloxyborane-amine complex intermediate involving three successive dehydrogenative additions of the acid to the amine-borane.

Mechanistically, we regard a triacyloxyborane-amine complex as the intermediate in the reaction. This complex, species IV in FIG. 3, is formed via three successive dehydrogenative additions of the acid to the amine-borane. Dehydrogenation was confirmed by quantifying the hydrogen evolved (~147 mL, 6 mmol, for a reaction using 2 mmol of amine-borane). To confirm the identity of the intermediate species, triacyloxyborane-amine complexes 4aa and 4cd formed by heating to 90-100° C. for 1-4 h, were isolated, almost quantitatively, and spectroscopically characterized (Scheme 2). The structure of 4aa was confirmed by X-ray crystallography.

Scheme 2. Postulated reaction pathway. Starting with carboxylic acid and amine-borane (I), progressing through dehydrogenation intermediates (II)/(III) to the active triacyloxyborane (IV) between 90-100° C. Heating (IV) to 150° C. allows intermediate complex (V) formation, which is broken upon MeOH addition to yield amide product and carboxylic acid-boric acid anhydride (VI) byproduct. The excess carboxylic acid is recovered from (VI) during aqueous work up of the product amide, additionally yielding an indeterminate byproduct (VII).

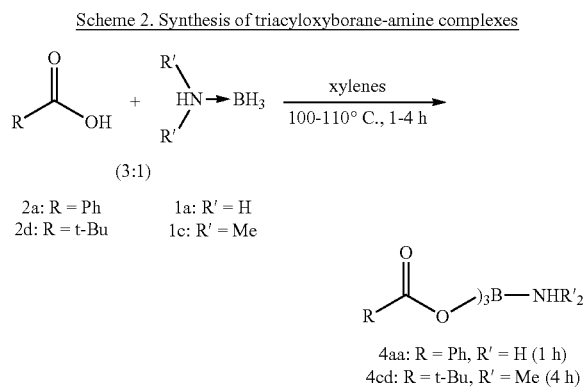

Figure 4:
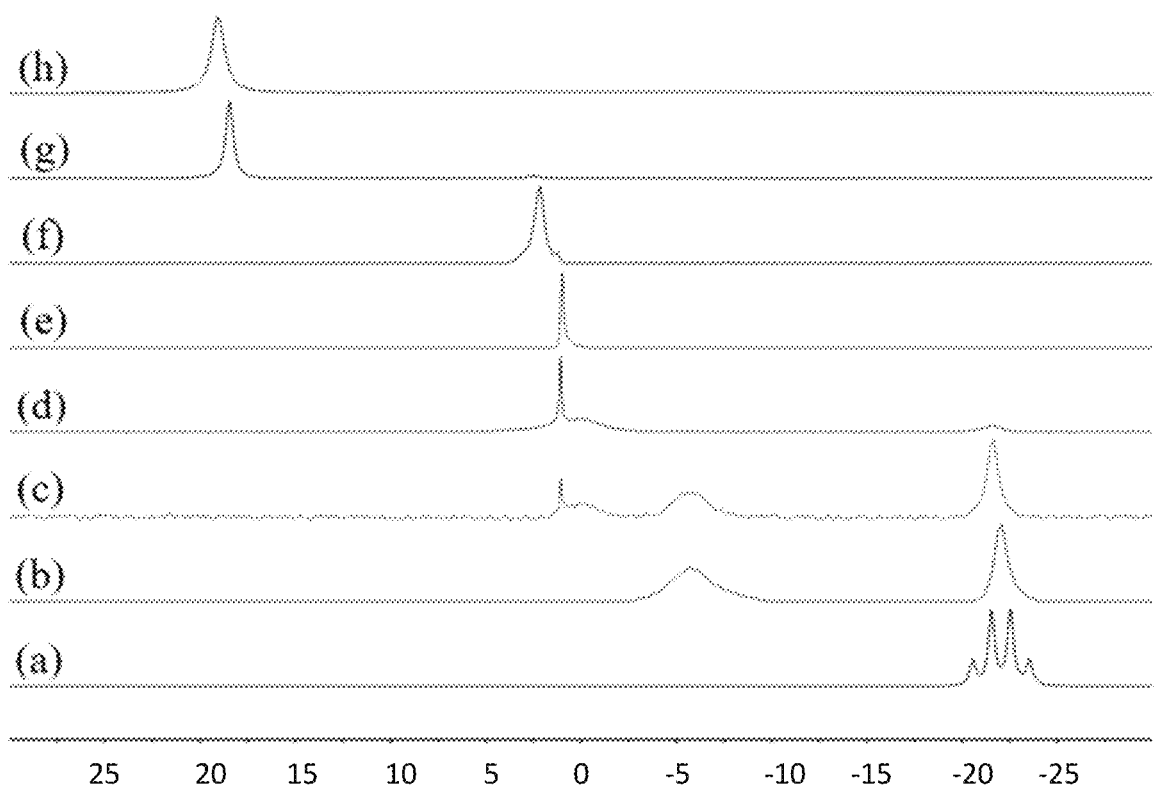
FIG. 4 depicts the spectra of the $^{11}B$ NMR monitoring of reaction progress. (a) Taken at 50° C., ammonia-borane starting material. (b) Taken at 60° C., B—H decoupled. (c) Taken at 70° C. (d) Taken at 80° C. (e) Taken at 90° C. (f) Taken at r.t. after 12 h at 150° C. (g) Taken at r.t., after methanol addition. (h) Taken after aqueous workup.

The reaction progress involving the formation of triacyloxyborane-amine complex 4aa from 1a and 2a, and subsequent amide production, monitored by $^{11}$B NMR spectroscopy, is shown in FIG. 4. The gradual formation of the triacyloxyborane-amine intermediate (FIG. 3, IV) is represented by the chemical shift at ~δ 1.1 ppm[33] in FIG. 4(e). The peaks corresponding to the mono- and diacyloxyborane intermediates seen at ~δ −5.8 and ~δ −0.1 ppm respectively (FIGS. 4(b) and 4(c), respectively), represents species II and III in FIG. 3. After complete conversion to the triacyloxyborane-amine complex, the mixture was heated to reflux for 12 h, at which point a second detectable intermediate was observed (~δ 2.0 ppm in FIG. 4(f)), tentatively postulated to be a complex where the carbonyl is coordinated to the boron (FIG. 3, V). This coordinate bond is broken immediately upon the addition of methanol, revealing a $^{11}$B NMR peak at ~δ 18 ppm (FIG. 4(g)).

We believe that this unisolated species is a carboxylic acid-boric acid anhydride (FIG. 3, VI) due to unsuccessful attempts at distillation of the initially postulated dimethyl hydrogen borate and trimethyl borate from the reaction mixture. Following the removal of the solvent the amide is recovered via acid/base extraction, leaving boric acid at δ ~19.0 ppm (FIG. 4 (h)) (FIG. 3, VII) and unused carboxylic acid in the aqueous fraction. Acidification of the aqueous fraction allows for a nearly quantitative (96%) recovery of the carboxylic acid unused in the reaction.

The possibility of an intra-versus intermolecular amine substitution was addressed by reacting equimolar amounts of two different triacyloxyborane-amine complexes 4aa and 4cd in refluxing xylenes. If the reaction was exclusively intramolecular, only two amide products (benzamide 3aa and N,N-dimethylpivalamide 3c), with the amine delivered to the carboxylic acid of the same complex, will be formed. The choice of the complex 4cd was made with the prospect of eliminating 3cd due to the earlier observation of the non-reaction of 1c with 2d to limit the product to only 3aa. However, if an intermolecular mechanism predominates, three amide products (3aa, 3ad, and 3ca) would be produced, with the amine delivered to the carbonyl of either complex.

The reaction products, analyzed using $^1$H NMR spectroscopy, showed a distinctive doublet (J=43.6 Hz) at ~δ 3.05 ppm, matching amide product 3ca. $^1$H NMR peaks corresponding to the benzamide (3aa) and pivalamide (3ad) were also detected. As expected, 3cd was not produced. These results indicate that the reaction is proceeding, at least partly, through an intermolecular, cross-complex reaction pathway.

In summary, we have developed a new, highly versatile procedure for the direct amidation of carboxylic acids using amine-boranes as bifunctional reagents, with good to excellent yields achieved for most of the 40 examples. Amine-boranes serve dual purpose; first as activators of the carboxylic acid, then as a carrier of the complexed amine. Amine-boranes containing borane incompatible functionalities allows the incorporation of halogen, heterocyclic, alkene, alkyne, nitro, thiol, and phenol functionalities into the amide products. This new methodology is superior to other amidation protocols, eliminating the use of hazardous and unstable reagents.[34-36] The absence of bulky, heteroatom containing coupling reagents[37,38] eliminates the need to perform difficult product purifications and improves atom economy. It requires no auxiliary base in the reaction, nor the use of dehydrating agents or azeotropic water removal. Most importantly, this protocol allows ready incorporation of gaseous and low-boiling amines into the amide products.

Experimental and $^{11}$B NMR spectroscopic studies reveal a plausible reaction pathway in which the amine of the intermediate triacyloxyborane-amine complex is delivered intermolecularly between complexes. The ready synthesis of a variety of amine-boranes allowing the preparation of a wide range of amide products makes this new methodology exceptional. Further unique applications of amine-boranes as dual-purpose reagents in organic synthesis are underway.

Those skilled in the art will recognize that numerous modifications can be made to the specific implementations described above. The implementations should not be limited to the particular limitations described. Other implementations may be possible.

It is intended that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES CITED (1) Brown, D. G.; Bostrom, J., Analysis of Past and Present Synthetic Methodologies on Medicinal Chemistry: Where Have All the New Reactions Gone? *J. Med. Chem.* 2016, 59, 4443-58.
(2) Pitzer, J.; Steiner, K., Amides in Nature and Biocatalysis *J. Biotechnol.* 2016, 235, 32-46.
(3) Bolton, E. K., Chemical Industry Medal. Development of Nylon *Ind. Eng. Chem.* 1942, 34, 53-58.
(4) Buckwalter, D. J.; Dennis, J. M.; Long, T. E., Amide-Containing Segmented Copolymers *Prog. Polym. Sci.* 2015, 45, 1-22.
(5) Garcia, J. M.; Garcia, F. C.; Serna, F.; de la Pena, J. L., High-Performance Aromatic Polyamides *Prog. Polym. Sci.* 2010, 35, 623-686.
(6) Zavradashvili, N.; Puiggali, J.; Katsarava, R., Artificial Polymers Made of Alpha-Amino Acids-Poly(Amino Acid)S, Pseudo-Poly(Amino Acid)S, Poly(Depsipeptide) S, and Pseudo-Proteins *Curr. Pharm. Des.* 2020, 26, 566-593.
(7) Rodriguez-Galan, A.; Franco, L.; Puiggali, J., Degradable Poly(Ester Amide)S for Biomedical Applications *Polym.* 2011, 3, 65-99.
(8) Crombie, L., Natural Product Chemistry and Its Part in the Defence against Insects and Fungi in Agriculture *Pestic. Sci.* 1999, 55, 761-774.
(9) Coleman, G. H.; Alvarado, A. M., Acetamide *Org. Synth.* 1923, 3, 3-5.
(10) Goossen, L. J.; Ohlmann, D. M.; Lange, P. P., The Thermal Amidation of Carboxylic Acids Revisited *Synthesis-Stuttgart* 2009, 160-164.
(11) Charville, H.; Jackson, D. A.; Hodges, G.; Whiting, A.; Wilson, M. R., The Uncatalyzed Direct Amide Formation Reaction—Mechanism Studies and the Key Role of Carboxylic Acid H-Bonding *Eur. J. Org. Chem.* 2011, 2011, 5981-5990.
(12) Jursic, B. S.; Zdravkovski, Z., A Simple Preparation of Amides from Acids and Amines by Heating of Their Mixture *Synth. Commun.* 1993, 23, 2761-2770.
(13) Bryan, M. C.; Dunn, P. J.; Entwistle, D.; Gallou, F.; Koenig, S. G.; Hayler, J. D.; Hickey, M. R.; Hughes, S.; Kopach, M. E.; Moine, G.; Richardson, P.; Roschangar, F.; Steven, A.; Weiberth, F. J., Key Green Chemistry Research Areas from a Pharmaceutical Manufacturers' Perspective Revisited *Green Chem.* 2018, 20, 5082-5103.
(14) Pattabiraman, V. R.; Bode, J. W., Rethinking Amide Bond Synthesis *Nature* 2011, 480, 471-479.
(15) Bode, J. W., Reinventing Amide Bond Formation. In *Inventing Reactions*, Goossen, L. J., Ed. 2013; Vol. 44, pp 13-33.
(16) de Figueiredo, R. M.; Suppo, J. S.; Campagne, J. M., Nonclassical Routes for Amide Bond Formation *Chem. Rev.* 2016, 116, 12029-12122.
(17) Nelson, P.; Pelter, A., Trisdialkylaminoboranes—New Reagents for Synthesis of Enamines and Amides *J. Chem. Soc.* 1965, 5142-&.
(18) Collum, D. B.; Chen, S. C.; Ganem, B., New Synthesis of Amides and Macrocyclic Lactams *J. Org. Chem.* 1978, 43, 4393-4394.
(19) Tang, P., Boric Acid Catalyzed Amide Formation from Carboxylic Acids and Amines: N-Benzyl-4-Phenylbutyramide *Org. Synth.* 2005, 81.
(20) Hall, D. G., Boronic Acid Catalysis *Chem. Soc. Rev.* 2019, 48, 3475-3496.
(21) Ishihara, K.; Ohara, S.; Yamamoto, H., 3,4,5-Trifluorobenzeneboronic Acid as an Extremely Active Amidation Catalyst *J. Org. Chem.* 1996, 61, 4196-4197.
(22) Sabatini, M. T.; Boulton, L. T.; Sheppard, T. D., Borate Esters: Simple Catalysts for the Sustainable Synthesis of Complex Amides *Sci. Adv.* 2017, 3.
(23) Huang, Z.; Reilly, J.; Buckle, R., An Efficient Synthesis of Amides and Esters Via Triacyloxyboranes *Synlett* 2007, 2007, 1026-1030.
(24) Tani, J.; Oine, T.; Inoue, I., Convenient Method of Amidation of Carboxylic-Acids Using Boron-Trifluoride Etherate *Synthesis-Stuttgart* 1975, 714-715.
(25) Ramachandran, P. V.; Drolet, M. P.; Kulkarni, A. S., A Non-Dissociative Open-Flask Hydroboration with Ammonia Borane: Ready Synthesis of Ammonia-Trialkylboranes and Aminodialkylboranes *Chem. Comm.* 2016, 52, 11897-11900.
(26) Rodriguez, J. R.; Hamann, H. J.; Mitchell, G. M.; Ortalan, V.; Pol, V. G.; Ramachandran, P. V., Three-Dimensional Antimony Nanochains for Lithium-Ion Storage *ACS Appl. Nano Mater.* 2019, 2, 5351-5355.
(27) Trapani, G.; Reho, A.; Latrofa, A.; Liso, G., Trimethylamine-Borane—a Useful Reagent in the One-Pot Preparation of Carboxylic Esters from Carboxylic-Acids *Synthesis-Stuttgart* 1990, 853-854.
(28) Ramachandran, P. V.; Kulkarni, A. S., Water-Promoted, Safe and Scalable Preparation of Ammonia Borane *Int. J. Hydrog. Energy* 2017, 42, 1451-1455.
(29) Noth, H.; Beyer, H., Beiträge Zur Chemie Des Bors, I. Darstellung Und Eigenschaften Der Alkylamin-Borane, $R_{3-N}h_nn.Bh_3$ *Chem. Ber. Recl.* 1960, 93, 928-938.
(30) Ramachandran, P. V.; Kulkarni, A. S.; Zhao, Y.; Mei, J., Amine-Boranes Bearing Borane-Incompatible Functionalities: Application to Selective Amine Protection and Surface Functionalization *Chem. Comm.* 2016, 52, 11885-11888.
(31) Burg, A. B.; Schlesinger, H. I., Hydrides of Boron Vii Evidence of the Transitory Existence of Borine ($BH_3$) Borine Carbonyl and Borane Trimethylammine *J. Am. Chem. Soc.* 1937, 59, 780-787.
(32) Tao, Y.; Widlicka, D. W.; Hill, P. D.; Couturier, M.; Young, G. R., A Scalable Synthesis of Ce-157119 Hcl Salt, an Sri/5-Ht2a Antagonist *Org. Process Res. Dev.* 2012, 16, 1805-1810.
(33) Brown, H. C.; Stocky, T. P., Selective Reductions. 24. Acyloxyboranes in Controlled Reaction of Carboxylic-Acids with Borane-Tetrahydrofuran—Acyloxyboranes as Intermediates in Fast Reduction of Carboxylic-Acids by Borane-Tetrahydrofuran *J. Am. Chem. Soc.* 1977, 99, 8218-8226.
(34) Adams, R.; Ulich, L. H., The Use of Oxalyl Chloride and Bromide for Producing Acid Chlorides, Acid Bromides or Acid Anhydrides. Iii *J. Am. Chem. Soc.* 1920, 42, 599-611.
(35) Klausner, Y. S.; Bodanszk, M, Azide Method in Peptide-Synthesis—Its Scope and Limitations *Synthesis-Stuttgart* 1974, 549-559.
(36) Froyen, P., The Conversion of Carboxylic-Acids into Amides Via Ncs Triphenylphosphine *Synth. Commun.* 1995, 25, 959-968.
(37) Valeur, E.; Bradley, M., Amide Bond Formation: Beyond the Myth of Coupling Reagents *Chem. Soc. Rev.* 2009, 38, 606-631.
(38) Montalbetti, C.; Falque, V., Amide Bond Formation and Peptide Coupling *Tetrahedron* 2005, 61, 10827-10852.

The invention claimed is:

1. A triacyloxyborane-amine complex comprising $[(R^3CO_2)_3-B^{-1}-N^{+1}H(R^1)R^2]$, wherein $R^3$ is an aryl, each of which is optionally substituted; $R^1$ and $R^2$ are, independently, hydrogen, an alkyl, or an aryl, wherein said alkyl or aryl are optionally substituted and said $R^1$ and $R^2$ are not both an aryl, an alkyl, or a hydrogen at the same time.

2. The triacyloxyborane-amine complex $[(R^3CO_2)_3-B^{-1}-N^{+1}H(R^1)R^2]$, according to claim 1, wherein said triacyloxyborane-amine complex $[(R_3CO_2)_3-B^{-1}-N^{+1}H(R^1)R^2]$ is manufactured as following:
  a. preparing an amine-borane $(R^1)R^2N-BH_3$ from an amine $R^1R^2NH$; wherein $R^1$ and $R^2$ are, independently, hydrogen, an alkyl, or an aryl, wherein said alkyl or aryl are optionally substituted and said $R^1$ and $R^2$ are not both an aryl, and alkyl, or a hydrogen at the same time;
  b. preparing a carboxylic acid $R^3COOH$, wherein $R^3$ is an aryl, which is optionally substituted;
  c. dissolving one equivalent of said amine-borane and about three equivalents of said carboxylic acid in xylenes or a compatible solvent to afford a reaction mixture; and
  d. heating said reaction mixture to about 90-100° C. for about 1 hour to afford said said triacyloxyborane-amine complex $[(R^3CO_2)_3-B^{-1}-N^{+1}H(R^1)R^2]$.

3. A product manufactured using the triacyloxyborane-amine complex according to claim 1.

4. An active pharmaceutical ingredient manufactured using the triacyloxyborane-amine complex according to claim 1.

\* \* \* \* \*